(12) United States Patent
Hamilton

(10) Patent No.: US 8,870,793 B2
(45) Date of Patent: Oct. 28, 2014

(54) METHOD AND APPARATUS FOR PROVIDING INFORMATION RELATED TO LABOR PROGRESS FOR AN OBSTETRICS PATIENT

(71) Applicant: Perigen Inc., Princeton, NJ (US)

(72) Inventor: Emily Hamilton, Verdun (CA)

(73) Assignee: Perigen Inc., Princeton, NJ (US)

( * ) Notice: Subject to any disclaimer, the term of this patent is extended or adjusted under 35 U.S.C. 154(b) by 0 days.

(21) Appl. No.: 14/036,188

(22) Filed: Sep. 25, 2013

(65) Prior Publication Data

US 2014/0221875 A1 Aug. 7, 2014

Related U.S. Application Data

(63) Continuation of application No. 11/330,942, filed on Jan. 12, 2006, now Pat. No. 8,636,676.

(60) Provisional application No. 60/687,855, filed on Jun. 7, 2005.

(51) Int. Cl.
*A61B 5/00* (2006.01)

(52) U.S. Cl.
USPC ......................................... 600/588

(58) Field of Classification Search
USPC ........................... 600/551, 588, 591
See application file for complete search history.

(56) References Cited

U.S. PATENT DOCUMENTS

| | | | |
|---|---|---|---|
| 3,989,034 A | 11/1976 | Hojaiban | |
| 5,042,503 A | 8/1991 | Torok et al. | |
| 5,069,218 A | 12/1991 | Ikeda | |
| 5,088,497 A | 2/1992 | Ikeda | |
| 5,483,970 A | 1/1996 | Rosenberg | |
| 6,200,279 B1 | 3/2001 | Paltieli | |
| 6,254,537 B1 | 7/2001 | Nguyen | |
| 6,423,016 B1 | 7/2002 | Hamilton et al. | |
| 6,669,653 B2 | 12/2003 | Paltieli | |
| 6,907,284 B2 | 6/2005 | Hamilton et al. | |
| 7,113,819 B2 | 9/2006 | Hamilton et al. | |
| 7,188,151 B2 | 3/2007 | Kumar et al. | |
| 7,207,941 B2 | 4/2007 | Sharf | |
| 2002/0083075 A1 | 6/2002 | Brummel et al. | |
| 2002/0193670 A1 | 12/2002 | Garfield et al. | |

(Continued)

FOREIGN PATENT DOCUMENTS

| | | |
|---|---|---|
| DE | 27 41 344 A1 | 3/1979 |
| DE | 37 29 760 A1 | 3/1989 |

(Continued)

OTHER PUBLICATIONS

European Search Report dated Jul. 25, 2007 in connection with EP Patent Application No. 07 29 0544, 7 pages.

(Continued)

*Primary Examiner* — Max Hindenburg

(57) ABSTRACT

A method and apparatus for evaluating labor progress during childbirth for an obstetrics patient are provided. A set of information data elements associated to an obstetrics patient are received, the set of information data elements including a cervical dilation measure and a level of descent indicator. The set of information data elements is processed to generate labor progress information associated to the obstetrics patient. The labor progress information conveys whether the level of descent indicator is within an expected range of levels of descent corresponding to the cervical dilation measure. A signal for causing the labor progress information to be provided to a user is then released.

35 Claims, 15 Drawing Sheets

(56) References Cited

U.S. PATENT DOCUMENTS

| | | | |
|---|---|---|---|
| 2003/0187364 A1 | 10/2003 | Hamilton et al. |
| 2003/0208128 A1 | 11/2003 | Hamilton et al. |
| 2004/0133115 A1 | 7/2004 | Hamilton et al. |
| 2004/0254430 A1 | 12/2004 | Hamilton |
| 2005/0049509 A1 | 3/2005 | Mansour et al. |
| 2005/0267376 A1 | 12/2005 | Marossero et al. |
| 2006/0015036 A1 | 1/2006 | Paltieli |
| 2006/0282019 A1 | 12/2006 | Hamilton |
| 2007/0255588 A1 | 11/2007 | Hamilton |
| 2008/0039744 A1 | 2/2008 | Hamilton |
| 2009/0240158 A1 | 9/2009 | Hamilton et al. |
| 2009/0259133 A1 | 10/2009 | Wolfberg et al. |

FOREIGN PATENT DOCUMENTS

| | | |
|---|---|---|
| DE | 198 22 250 A1 | 11/1999 |
| EP | 0 286 731 A1 | 10/1988 |
| EP | 0 306 915 A1 | 3/1989 |
| EP | 0 808 603 A2 | 11/1997 |
| EP | 1 161 921 A2 | 12/2001 |
| EP | 1 852 065 A1 | 11/2007 |
| EP | 1 852 065 B1 | 9/2011 |
| WO | 01/93752 A2 | 12/2001 |
| WO | 2004/041059 A2 | 5/2004 |
| WO | 2005/015451 A1 | 2/2005 |

OTHER PUBLICATIONS

European Search Report dated Jul. 25, 2007 in connection with EP Patent Application No. 07 29 0533, 7 pages.
International Search Report mailed on Mar. 30, 2009 in connection with International Patent Application No. PCT/CA2008/002134, 3 pages.
Written Opinion of the International Searching Authority mailed on Mar. 30, 2009 in connection with International Patent Application No. PCT/CA2008/002134, 4 pages.
Written Opinion of the International Searching Authority mailed on Jul. 5, 2006 in connection with International Patent Application No. PCT/CA2006/000417, 7 pages.
Office Action issued by the United States Patent and Trademark Office on Sep. 18, 2009 in connection with U.S. Appl. No. 11/416,281, 8 pages.
Office Action issued by the European Patent Office on Jun. 2, 2008 in connection with EP Patent Application No. 07 29 0544, 2 pages.
Office Action issued by the European Patent Office on Jun. 3, 2008 in connection with EP Patent Application No. 07 29 0533, 2 pages
Hamilton, E. et al, "A comprehensive labour surveillance system", Journal of Perinatal Medicine, vol. 15, Supplement 1, p. 144 (1987).
"World Health Organisation Partograph in management of labour", The Lancet, vol. 343, Jun. 4, 1994, pp. 1399-1404.
World Health Organisation, Division of Family Health, Geneva, Maternal Health and Safe Motherhood Programme, "The Partograph: The Application of the WHO Partograph in the Management of Labour", Copyright World Health Organisation, Geneva, Switzerland, 1994, pp. i-xviii and pp. 1-7.
Hamilton, E. et al, "Labor Pains, Unraveling the Complexity of OB Decision Making", Crit Care Nurs Q, 2006, vol. 29, No. 4, pp. 342-353.
Declaration of Non-Establishment of International Search Report mailed on Jul. 5, 2006 in connection with International Patent Application No. PCT/CA2006/000417, 2 pages.
International Preliminary Report on Patentability issued on Jun. 15, 2010 in connection with International Patent Application No. PCT/CA2008/002134, 6 pages.
Office Action issued by the United States Patent and Trademark Office on Mar. 18, 2010 in connection with U.S. Appl. No. 11/416,281, 18 pages.
Office Action issued by the United States Patent and Trademark Office on Apr. 14, 2010 in connection with U.S. Appl. No. 11/716,496, 39 pages.
Office Action issued by the United States Patent and Trademark Office on Oct. 3, 2011 in connection with U.S. Appl. No. 12/285,617, 6 pages.
Office Action issued by the United States Patent and Trademark Office on Apr. 5, 2012 in connection with U.S. Appl. No. 11/416,281, 22 pages.
Examiners Report (i.e., Office Action) issued by the Canadian Intellectual Property Office on Jun. 8, 2012 in connection with Canadian Patent Application No. 2,610,393, 5 pages.
Examiner's Report (i.e., Office Action) issued by the Canadian Intellectual Property Office on Jul. 24, 2012 in connection with Canadian Patent Application No. 2,545,339, 3 pages.
Office Action issued by the United States Patent and Trademark Office on Feb. 4, 2013 in connection with U.S. Appl. No. 11/416,281, 16 pages.
Office Action issued by the United States Patent and Trademark Office on Mar. 18, 2013 in connection with U.S. Appl. No. 12/747,022, 13 pages.
Examiner's Report (i.e., Office Action) issued by the Canadian Intellectual Property Office on May 3, 2013 in connection with Canadian Patent Application No. 2,610,393, 6 pages.
Office Action issued by the United States Patent and Trademark Office on Jun. 11, 2013 in connection with U.S. Appl. No. 11/416,281, 17 pages.
Office Action issued by the United States Patent and Trademark Office on Jun. 19, 2013 in connection with U.S. Appl. No. 11/716,496, 37 pages.
Office Action issued by the United States Patent and Trademark Office on Jun. 20, 2013 in connection with U.S. Appl. No. 12/747,022, 16 pages.
H.N. Sallam et al., "Mathematical relationships between uterine contractions, cervical dilatation, descent and rotation in spontaneous vertex deliveries", International Journal of Gynecology & Obstetrics, vol. 64, Issue 2, 1 Feb. 1999 (Jan. 2, 1999), pp. 135-139.
Emanuel A. Friedman, M.D., "The Graphic Analysis of Labor", American Journal of Obstetrics & Gynecology, vol. 68, 1954, pp. 1568-1575.
Office Action issued by the United States Patent and Trademark Office on May 17, 2010 in connection with U.S. Appl. No. 11/330,942, 7 pages.
Office Action issued by the United States Patent and Trademark Office on Jul. 26, 2010 in connection with U.S. Appl. No. 11/330,942, 11 pages.
Office Action issued by the United States Patent and Trademark Office on Dec. 21, 2010 in connection with U.S. Appl. No. 11/716,496, 36 Pages.
Office Action issued by the United States Patent and Trademark Office on Feb. 7, 2011 in connection with U.S. Appl. No. 11/416,281, 23 Pages.
Office Action issued by the United States Patent and Trademark Office on Feb. 7, 2011 in connection with U.S. Appl. No. 11/330,942, 11 Pages.
Office Action issued issued by the United States Patent and Trademark Office on Mar. 1, 2011 in connection with U.S. Appl. No. 12/285,617, 7 Pages.
Office Action issued by the European Patent Office on Feb. 23, 2011 in connection with European Patent Application No. 2007290544.1, 4 pages.
Notice of Allowance issued by the European Patent Office on Mar. 24, 2011 in connection with European Patent Application No. 2007290533.4, 5 pages.
Notice of Allowance issued by the European Patent Office on Jul. 11, 2013 in connection with European Patent Application No. 2007290544.1, 5 pages.
Zhang, Jun et al., "Reassessing the labor curve in nulliparous women", AJOG (2002), vol. 187, No. 4, pp. 824-828.

FIG. 3

METHOD AND APPARATUS FOR PROVIDING INFORMATION RELATED TO LABOR PROGRESS FOR AN OBSTETRICS PATIENT

CROSS-REFERENCE TO RELATED APPLICATIONS

This application is a continuation of U.S. patent application Ser. No. 11/330,942 filed Jan. 12, 2006, which in turn claims the benefit of priority on the previously filed U.S. provisional application entitled "Method and apparatus for providing information related to labor progress for an obstetrics patient" filed on Jun. 7, 2005 by Emily Hamilton and which was assigned Ser. No. 60/687,855. The contents of the above applications are incorporated herein by reference.

FIELD OF THE INVENTION

The present invention relates generally to the field of obstetrics, and more specifically to a method and apparatus for providing information related to labor progress for an obstetrics patient. This invention can be used to assist decision making in clinical medicine.

BACKGROUND OF THE INVENTION

The labor of childbirth is the process by which uterine contractions cause the fetus and placenta to be expelled from the uterus and birth canal. Rhythmic contractions of the uterine muscle create a force that pushes the fetus against the opening of the uterus, commonly referred to as the cervix. The cervix is a tubular structure that is firm and closed during pregnancy, keeping the baby and membranes protected inside the uterus. At term, the cervix softens and in labor the continuing pressure of the fetus on the cervix causes it to shorten (efface) and to open (dilate) up to 10 centimeters. As the cervix completely effaces and dilates, the contractions and the mother push the baby through the birth canal. The level of descent of the baby through this passage is referred to as station. Contractions are the forces that promote cervical dilation. Resistance of the cervix and the birth canal are the opposing forces to the contractions. In addition, the resistance of the cervix changes as it becomes more effaced and more dilated.

Commonly, the effacement, the dilation, the frequency and strength of the contractions and the station are measured clinically during labor and are used by the doctors to determine if the labor is progressing normally. Generally, if the doctor determines that the labor is progressing normally, the delivery is permitted to continue through the birth canal. However, if the doctor determines that the labor is not progressing normally, a cesarean section is effected to complete the delivery. Cesarean deliveries are associated with maternal morbidity and an increase in the risk of complications during the current and the subsequent pregnancies. Cesarean deliveries are also more expensive than vaginal births.

Due to the very large number of possible combinations of values for the dilation, the effacement, the frequency of the contractions and the station, the evaluation of labor progress is a difficult task for doctors. Unlike most surgical procedures, there is no suitable postoperative confirmation of the preoperative diagnosis that can be used to validate the doctor's decision.

One of the most commonly used guidelines for assessing the progress of labor during the first stage of labor is to evaluate the level of descent of the baby, or station, with respect to time. Intuitively, if the level of descent of the baby does not progress as time goes by, there may be cause for concern. Another guideline is to observe the dilation of the cervix during the first stage of labor with respect to time. Similarly, if dilation of the cervix does not progress as time goes by, there may also be cause for concern. For more information regarding the above, the reader is invited to refer to J. Zhang et al., "Reassessing the labor curve in nulliparous women", Transactions of the twenty-second annual meeting of the society for maternal-fetal medicine, American Journal of Obstetrics and Gynecology, Volume 187, Number 4, October 2002, pp. 824-828. The contents of the above document are incorporated herein by reference.

A deficiency associated with existing methods, such as the ones described in the above noted publication, is that they do not adequately quantify labor progression. It will be appreciated that certain women take 4 hours to complete the first stage of labor while other women take 24 hours or more to complete the first stage. The above guidelines provide a general description of the average and range of observed rates of change in cervical dilation and fetal descent over time. These rates reflect an average response to an average set of conditions. They do not provide a method for discriminating if the unusually slow progression is due to conditions such as poor uterine contraction strength, or high cervical compliance or to a misfit between the size of the baby and the size of the mother. In practice, the clinical staff relies to a great extent on its knowledge and experience, rather than on such absolute measurements in order to make decisions as to whether an intervention should be considered. While doctors and nurses are trained and presumably competent in their ability to assess labor progression, there can be differences of interpretation that may result in either delayed or excessive rates of intervention depending upon the caregivers. As such, due to the lack of objective and reliable data, variations in judgment or management are more prone to occur; the more extreme causing harm to mother and or baby. Further, in the absence of such objective and reliable data and when the actions of the health care team are evaluated retrospectively, the reviewers who may be judges and jurors must also make subjective interpretations about the adequacy of the labor progression and the reasonableness of the clinical opinions at the time. The current methods do not provide a suitable indication of normal and abnormal labor progress, which considers specific and changeable labor conditions.

Therefore, in the context of the above, there is a need to provide a method and apparatus for providing information related to labor progress for an obstetrics patient that alleviates at least in part problems associated with the existing methods and devices.

SUMMARY OF THE INVENTION

In accordance with a broad aspect, the present invention provides a method for evaluating labor progress during childbirth for an obstetrics patient. The method comprises receiving a set of information data elements associated to an obstetrics patient including a cervical dilation measure and a level of descent indicator. The method also includes processing the set of information data elements to generate labor progress information associated to the obstetrics patient. The labor progress information conveys whether the level of descent indicator is within an expected range of levels of descent corresponding to the received cervical dilation measure. The method also includes causing the labor progress information to be provided to a user.

In a specific example of implementation, the labor progress information conveys the level of descent indicator in relation to the expected range of levels of descent.

In a first specific example of implementation, the cervical dilation measure is an expected cervical dilation measure associated to the obstetrics patient. The expected range of levels of descent is derived at least in part on the basis of the expected cervical dilation measure. The labor progress information is caused to be conveyed in either graphical format or text format. In a specific implementation where the labor progress information is caused to be conveyed in graphical format, the graphical format includes a chart having a horizontal axis and a vertical axis, the horizontal axis being associated to time and the vertical axis being associated to levels of descent.

In a second specific example of implementation, the cervical dilation measure is an observed cervical dilation measure associated to the obstetrics patient. The observed cervical dilation measure is obtained during a conventional cervical examination. The expected range of levels of descent is derived at least in part on the basis of the observed cervical dilation measure. The method also includes providing a plurality of expected ranges of levels of descent, each expected range of levels of descent corresponding to a respective cervical dilation and causing the plurality of expected ranges of levels of descent to be conveyed to a user. In a specific implementation, the plurality of expected ranges of levels of descent is derived from data associated to a reference population. The labor progress information is caused to be conveyed in either text format or graphical format. In a specific implementation where the labor progress information is caused to be conveyed in graphical format, the graphical format includes a chart having a horizontal axis and a vertical axis, the horizontal axis being associated to cervical dilation measures and the vertical axis being associated to levels of descent.

In specific implementations, the labor progress information may be conveyed on a display screen or may be presented in printed format.

In a specific example of implementation, the method further includes generating intervention policy information when the level of descent indicator is outside the expected range of levels of descent and causing the intervention policy information to be provided to a user. In a non-limiting example of implementation, the intervention policy information may indicate that a cesarean section is recommended when the level of descent indicator is outside the expected range of levels. The possible intervention policy information may include, without being limited to medications to increase uterine contractions, maternal positional changes to promote rotation and descent of the baby's head or cesarean section.

In accordance with another broad aspect, the present invention provides an apparatus for evaluating labor progress during childbirth for an obstetrics patient in accordance with the above-described method.

In accordance with yet another broad aspect, the present invention provides a computer readable storage medium including a program element suitable for execution by a computing apparatus. The computing apparatus has a memory unit and a processor in communication with the memory unit for evaluating labor progress during childbirth for an obstetrics patient in accordance with the above-described method.

In accordance with yet another broad aspect, the present invention provides a system for monitoring an obstetrics patient. The system comprises an interface for receiving a set of information data elements associated to an obstetrics patient, the set of information data elements including a cervical dilation measure and a level of descent indicator. The system further comprises an apparatus for generating labor progress information in accordance with the above-described method, the apparatus being in communication with the interface. The system further comprises an output unit in communication with the apparatus for conveying the labor progress information to a user.

In specific examples of implementation, the interface may be any suitable input device for receiving a set of information data elements associated to an obstetrics patient, such as, but not limited to a keyboard, a pointing device, a touch sensitive screen, and a voice recognition unit.

In specific examples of implementation, the output unit may be any suitable output device for providing labor progress information to a user, such as, but not limited to a display screen and a printing device.

In accordance with yet another broad aspect, the present invention provides a client-server system for evaluating labor progress during childbirth for an obstetrics patient. The client-server system includes a client system and a server system operative to exchange messages over a data network. The server system stores a program element for execution by a CPU and including first, second, third and fourth program element components. The first program element component is executed on the server and is for receiving a set of information data elements associated to an obstetrics patient, the set of information data elements including a cervical dilation measure and a level of descent indicator. The second program element component is executed on the server system and is for processing the set of information data elements to generate labor progress information associated to the obstetrics patient. The labor progress information conveys whether the level of descent indicator is within an expected range of levels of descent, the expected range of levels of descent corresponding to the cervical dilation measure. The third program element component is executed on the server system and is for sending messages to the client system for causing the client system to convey the labor progress information. The fourth program element component is executed on the client server system and is for receiving a message from the server system for conveying the labor progress information to a user.

In accordance with another broad aspect, the invention provides a method for evaluating labor progress during childbirth for an obstetrics patient. The method includes obtaining a set of information data elements associated to an obstetrics patient, the set of information data elements including a cervical dilation measure and a level of descent indicator. The method also includes transmitting the set of information data elements to a remote computing apparatus, the remote computing apparatus being operative for generating labor progress information associated to the obstetrics patient. The labor progress information conveys whether the level of descent indicator is within an expected range of levels of descent, where the expected range of levels of descent corresponds to the cervical dilation measure. The method also includes receiving data from the remote computing apparatus, the data conveying the labor progress information and causing the labor progress information to be provided to a user.

These and other aspects and features of the present invention will now become apparent to those of ordinary skill in the art upon review of the following description of specific embodiments of the invention in conjunction with the accompanying drawings.

BRIEF DESCRIPTION OF THE DRAWINGS

In the accompanying drawings:

FIG. 3 shows a user interface, in accordance with a non-limiting example of implementation of the present invention for use in the apparatus shown in FIG. 1, for receiving a set of information data elements associated to an obstetrics patient;

Other aspects and features of the present invention will become apparent to those ordinarily skilled in the art upon review of the following description of specific embodiments of the invention in conjunction with the accompanying figures.

DETAILED DESCRIPTION

Figure 1:
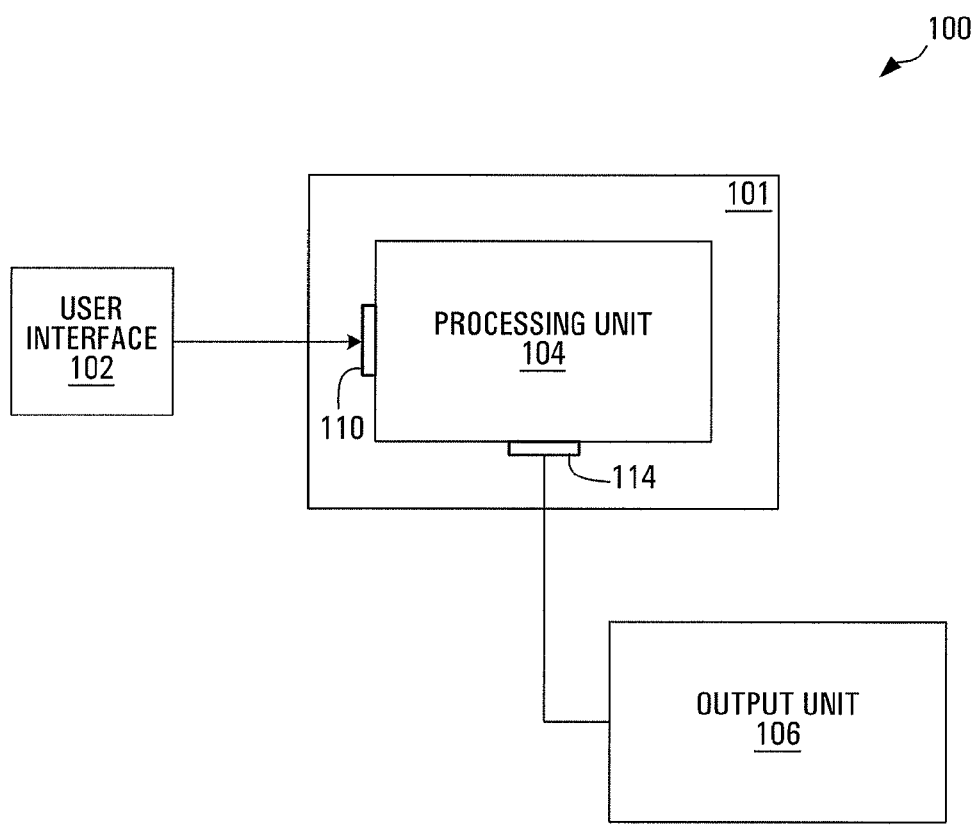
FIG. 1 shows a high-level functional block diagram of a system for monitoring an obstetrics patient in accordance with a specific example of implementation of the present invention.

With reference to FIG. 1, there is shown a configuration of a system 100 for monitoring an obstetrics patient. The system 100 comprises a user interface 102, an apparatus 101 including a processing unit 104, and an output unit 106.

The user interface 102 includes any one or a combination of a keyboard, a pointing device, a touch sensitive surface, a speech recognition unit or any other suitable device allowing information to be entered by a user. Alternatively, the user interface 102 may be in the form of a data input device such as, but not limited to, a disk drive, CD-ROM, a port connected to a data stream and flash memory. The user interface 102 enables a user to provide a set of information data elements associated to a certain obstetrics patient.

Figure 2:
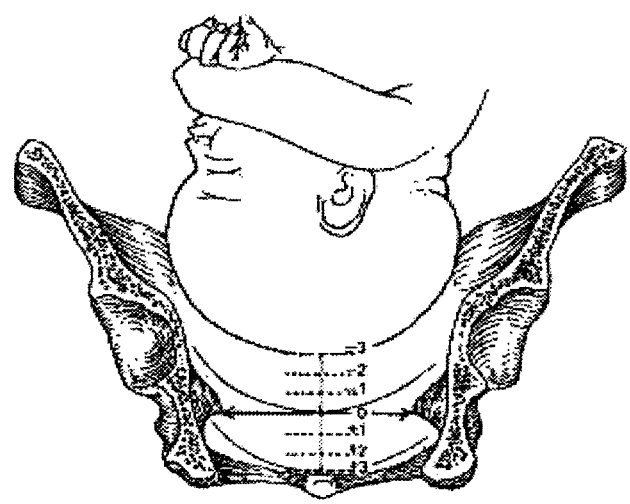
FIG. 2 is a diagram illustrating the use of stations as a measure of the level of descent in accordance with a specific example of implementation of the invention.

The set of information data elements includes a cervical dilation measure and a level of descent indicator. In a non-limiting example of implementation, the level of descent indicator is expressed as a station. Station refers to a measure in centimeters of the distance between the leading bony edge of the presenting fetal part and the maternal ischial spines, which are palpable prominences on one of the bony borders of the birth canal. The clinician can feel these landmarks during a pelvic examination and thereby estimates this distance. When the fetal part is above the spines the notation is negative, when at the spines the notation is 0, and when the baby is lower or closer to being born the notation is positive. FIG. 2 of the drawings illustrates the use of stations as a measure of the level of descent. It will be appreciated that manners for expressing the level of descent of a fetus other than the use of stations may be used without detracting from the spirit of the invention.

Figure 3:
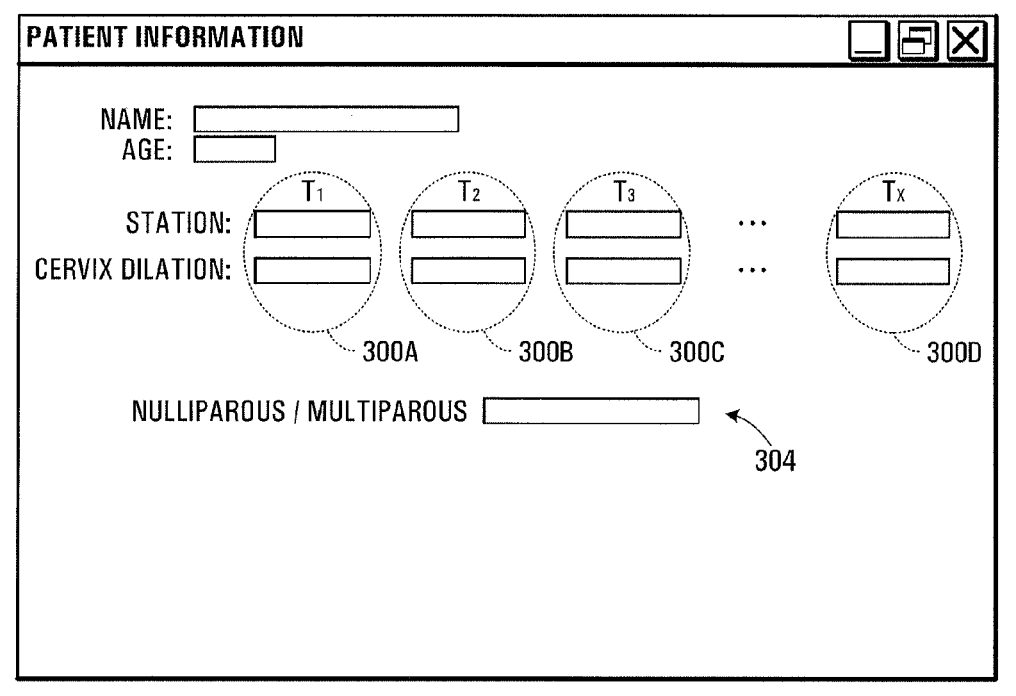

FIG. 3 of the drawings depicts a non-limiting example of a user interface for receiving a set of information data elements associated to a certain obstetrics patient. In the specific example depicted, the set of information data elements includes a previous vaginal birth indicator (nulliparous or multiparous patient) 304 and a plurality of level of descent indicator/cervical dilation measure pairs 300A-D, each pair 300A-D being indicative of measurements taken at a given time during the first stage of labor.

Optionally, the set of information data elements also includes, without being limited to, information derived from a maternal age component, a gestational age indicator, and maternal race. Optionally still, the set of information data elements may include information derived from labor information elements. Examples of labor information elements include, without being limited to, induction of labor and epidural anaesthesia. Other suitable information data elements may also be provided through user interface 102 without detracting from the spirit of the invention.

The apparatus 101 receives the set of information data elements including the cervical dilation measure and the level of descent indicator. The apparatus 101 processes the set of information data elements to generate labor progress information associated to the obstetrics patient. In the specific embodiment shown in FIG. 1, apparatus 101 includes a processing unit 104, an input 110 and an output 114. Input 110 is operative for receiving signals from the user interface 102 indicative of a set of information data elements associated to the obstetrics patient. As shown in FIG. 1, the processing unit 104 is in communication with input 110 for receiving the signal or signals indicative of a set of information data elements associated to the obstetrics patient. As will be described in more detail below, on the basis of the signal or signals received at input 110, the processing unit 104 is operative to generate labor progress information associated to the obstetrics patient. The labor progress information conveys whether the level of descent indicator is within the expected range of levels of descent corresponding to the cervical dilation measure.

The apparatus 101 releases at output 114 a signal for causing output unit 106 to convey the labor progress information to a user. The output unit 106 may be in the form of any suitable device for conveying information to the physician or other health care professional. In a specific example of implementation, the output unit 106 can include a display screen, or in an alternative example of implementation, the output unit 106 can include a printing device for displaying the data in printed form.

In a specific example, the system 100 is used during the first stage of labor to monitor whether the level of descent of the fetus is within an expected range of levels of descent for a given cervical dilation. Multiple measurements of the level of descent and of the cervical dilation are obtained from an obstetrics patient over time to track the progression of the level of descent against the cervical dilation. This information is presented to the health care practitioner in graphical format or in text format. This information may be used in combination with a hospital policy, to assist a physician in determining whether the labor of a given obstetric patient is progressing normally or whether intervention is advisable.

Alternatively, in a second specific implementation, the system 100 may be used after a delivery to assess whether the progression of the levels of descent against the cervical dilations was within expected ranges of levels of descent during the first stage of labor. In a manner similar to that in the first implementation, multiple measurements of the level of descent and of the cervical dilation are obtained from a record associated to an obstetrics patient to track over time the progression of the level of descent against the cervical dilation. Such information may be useful in the context of an insurance claim, a legal malpractice suit or another situation in which a physician's actions or decisions are being questioned. For example, this information may be used in combination with other data to determine whether a physician respected certain intervention policies and best practice guidelines.

The processing unit 104 in apparatus 101 will now be described in greater detail below with reference to FIG. 4 in a first embodiment and with reference to FIG. 9 in a second embodiment.

Processing Unit 104

First Embodiment

In a first specific embodiment, the processing unit 104 is adapted to derive an expected range of levels of descent at least in part on the basis of a cervical dilation measure, the cervical dilation measure being an observed cervical dilation measure. The observed cervical dilation measure is obtained from a pelvic examination.

Figure 4:
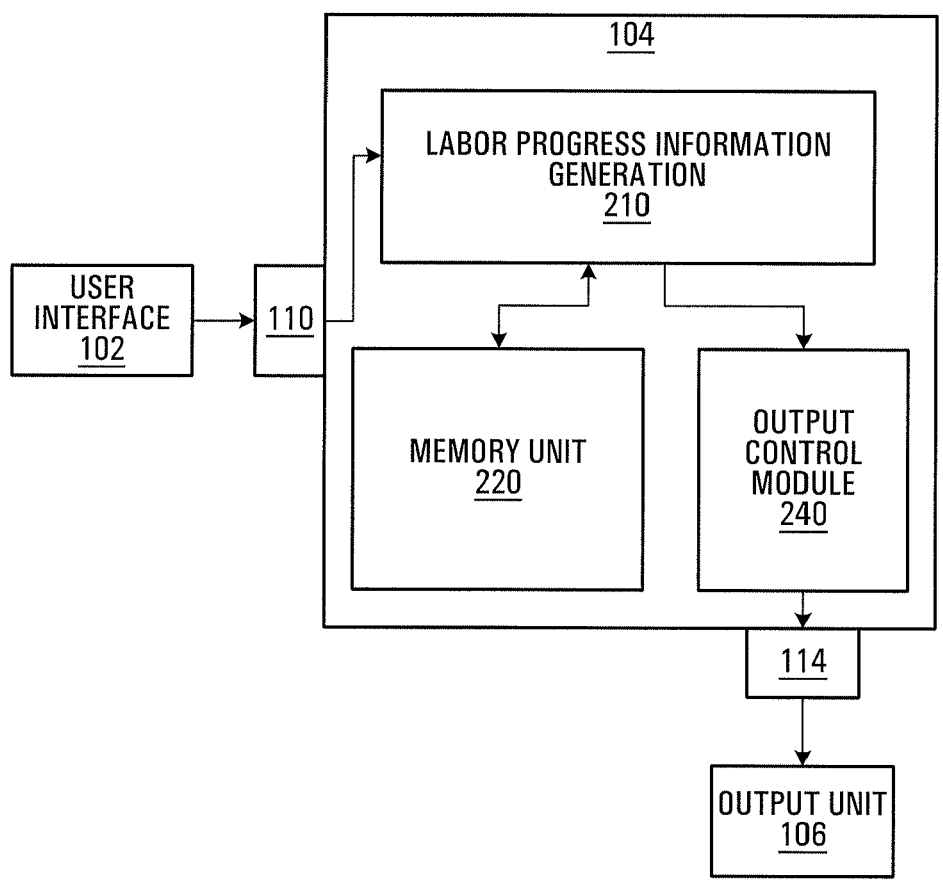
FIG. 4 shows a functional block diagram of an apparatus for generating labor progress information suitable for use in the system depicted in FIG. 1 in accordance with a first specific example of implementation of the present invention.

As shown in FIG. 4, the processing unit 104, in accordance with a first specific embodiment, includes a labor progress generation module 210, a memory unit 220 and an output control module 240.

Memory unit 220 stores a plurality of expected ranges of levels of descent, each expected range of levels of descent corresponding to a respective cervical dilation. In a specific implementation, the plurality of expected ranges of levels of descent corresponding to respective cervical dilations are stored in the form of a normogram of stations conveying for each cervical dilation a mean expected level of descent and a standard deviation of the level of descent. The manner in which the normogram is derived will be described later on in the specification. Alternatively, memory unit 220 stores a mathematical model allowing to compute a plurality of expected ranges of levels of descent on the basis of a cervical dilation. Optionally, memory unit 220 stores multiple sets of mappings between the cervical dilations and the expected range of levels of descent, each set of mappings being associated to mothers having certain characteristics. In a specific example, memory unit 220 stores one set of mappings between the cervical dilations and the expected range of levels of descent for nulliparous women and another set of mappings for multiparous women.

It will be appreciated that although memory unit 220 has been shown to be an integral parts of processing unit 104, memory unit 220 may be an external component to processing unit 104 without detracting from the spirit of the invention.

Labor Progress Information Generation Unit 210

For an observed level of descent indicator/cervical dilation pair received at input 110, the labor progress generation module 210 is adapted to generate data conveying whether the observed level of descent indicator is within the expected range of levels of descent corresponding to the observed cervical dilation. The expected range of levels of descent corresponding to the cervical dilation is derived from information stored in memory unit 220.

Figure 5:
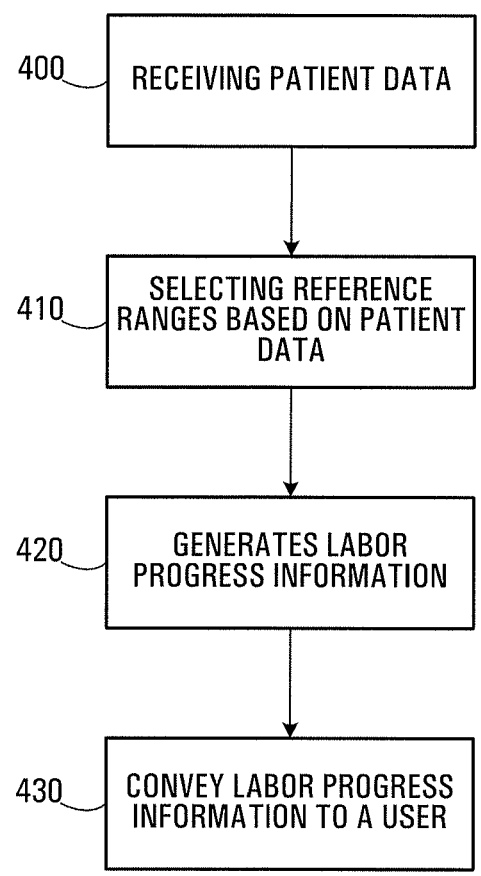
FIG. 5 is a flow diagram of a process in accordance with a specific example of implementation of the present invention for generating labor progress information conveying whether the level of descent associated to an obstetrics patient is within an expected range of levels of descent.

FIG. 5 of the drawings depicts a process implemented by the labor progress generation module 210 in accordance with a specific example of implementation of the invention.

At step 400, patient data is received by the labor progress generation module 210. The patient data includes a set of information data elements associated to an obstetrics patient including a cervical dilation measure and an observed level of descent indicator. Optionally, the patient data may also include, without being limited to, a previous vaginal birth indicator (nulliparous or multiparous patient), whether or not an epidural was given, maternal age component, a maternal diabetes indicator, gestational age indicator, maternal weight, maternal height and maternal race.

At step 410, in the specific example of implementation where the memory unit 220 includes multiple sets of mappings between the cervical dilations and the expected range of levels of descent, the labor progress generation module 210 selects a set of mappings on the basis certain patient characteristics (previous vaginal birth indicator (nulliparous or multiparous patient), whether or not an epidural was given, maternal age component, a maternal diabetes indicator, gestational age indicator, maternal weight, maternal height and maternal race). It will be appreciated that, in implementations where the mapping between the cervical dilations and the expected range of levels of descent is not differentiated on the basis of patient characteristics, step 410 may be omitted.

At step 420, the labor progress generation module 210 makes use of the information in memory unit 220 and the set of information data elements received in order to generate labor progress information. The labor progress information conveys whether the observed level of descent indicator is within the expected range of levels of descent for the observed cervical dilation measure. The expected range of levels of descent for the observed cervical dilation measure is obtained from the memory unit 220.

Optionally, the labor progress information conveys multiple observations taken over time of levels of descent and cervical dilation measures such as to convey for each of the levels of descent whether it was within the expected range of levels of descent for the corresponding cervical dilation measure. By taking these measures over time, the labor progress information also conveys the trend of the levels of descent with respect to the cervical dilations.

Optionally still, the labor progress information conveys a divergence between the observed level of descent and the expected range of levels of descent. More specifically, the labor progress generation module 210 is adapted for computing the divergence between the observed level of descent and the mean expected level of descent for a given cervical dilation and for conveying this divergence to the user. The divergence of the observed level of descent from the mean expected level of descent may be expressed in absolute terms or in terms of a ranking.

As a first example using the divergence expressed in absolute terms, take a mean expected level of descent for a 3 cm dilation to be −1.7 and the observed level of descent to be −1.0, then the divergence is expressed in absolute terms as:

Observed−expected=observed divergence

−1.0−(−1.7)=+0.7

The above divergence of +0.7 indicates that the descent is progressing faster that the mean. It will be apparent however that this value does not necessarily convey sufficient information to a physician without also providing what the spread or standard deviation of the expected level of descent as observed in a reference population.

As a second example, take a mean expected level of descent for a 3 cm dilation to be −1.7, a standard deviation of 0.9 and the observed level of descent to be −1.0. Using the standard deviation of the expected level of descent, the percentile ranking of the observed level of descent can be computed.

Optionally still, the labor progress generation module 210 is further adapted for generating intervention policy information when the level of descent indicator is outside the expected range of levels of descent. The policy is generally determined by a health care institution or professional association, usually a hospital, which determines a certain level of care. In a non-limiting example of implementation, the intervention policy information may indicate that a cesarean section is recommended when the level of descent indicator is outside the expected range of levels. The possible intervention policy information may include, without being limited to, instructions to perform or to avoid rupturing the membranes, medications to increase uterine contractions, maternal positional changes to promote rotation of the baby's head or cesarean section.

At step 430, the labor progress information, and optionally the intervention policy information, are released to the output control module 240 and conveyed to a user.

In a first specific example of implementation, the labor progress generation module 210 is adapted to generate data for causing labor progress information to be conveyed in graphical format.

Figure 6A:
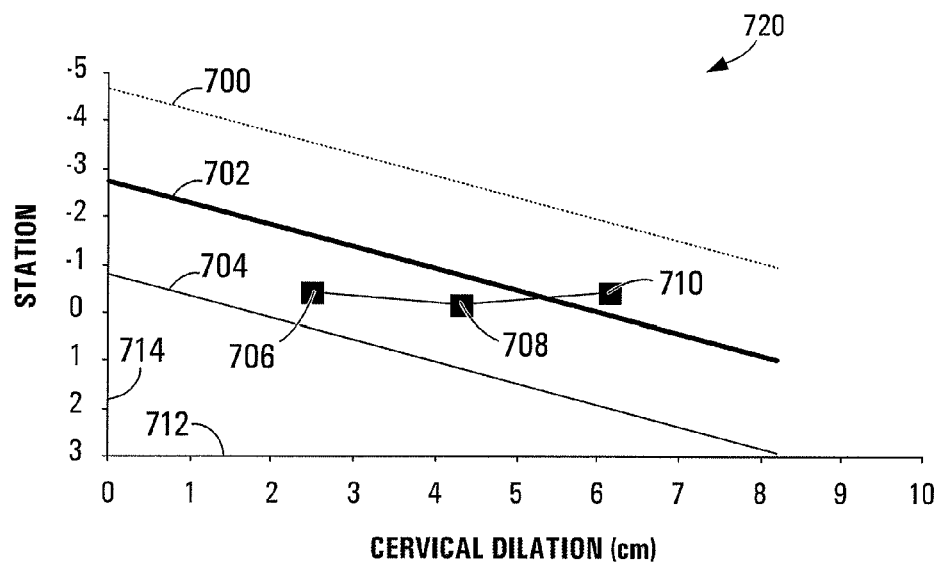
FIG. 6a shows a station curve conveying expected ranges of station (level of descent) versus cervical dilations in accordance with a specific example of implementation of the present invention.

FIG. 6a of the drawings shows a specific example of labor progress information conveyed in graphical format in accordance with a specific example of implementation. In the chart 720 depicted in FIG. 6a, horizontal axis 712 is associated to cervical dilation measures and vertical axis 714 is associated to levels of descent, in this example expressed in the form of stations. The observed levels of descent at given cervical dilations associated to the obstetrics patient are plotted on the chart 720 as items 706 708 and 710. Optionally, the different items 706 708 and 710 are connected to one another with a curve such as to visually show the progression of the levels of descent. The chart 720 also shows the expected ranges of levels of descent corresponding to cervical dilations that are derived from information stored in memory unit 220. More specifically, curves defining an upper boundary 700 and a lower boundary 704 convey the ranges of expected levels of descent for various cervical dilations. Optionally, the mean value of the level of descent is also shown in the chart 720 as a curve 702.

Advantageously, the information conveyed by the above-described chart can be used by a physician or other health care practitioner to assess whether the baby is descending through the birth canal normally during labor. The curves defining the upper boundary 700 and the lower boundary 704 convey the ranges of expected levels of descent for various cervical dilations during normal labors. As will be described later on in the specification, the upper boundary 700 and lower boundary 704 may be set according to various factors. In a non-limiting implementation, the upper boundary 700 and lower boundary 704 are set to correspond to the 95$^{th}$ and 5$^{th}$ percentile of a normal distribution of levels of descent for a each increment of cervical dilation as observed in a reference population. The physician can compare visually a mother's observed level of descent to the range of expected ones for a cervical dilation value.

Figure 6B:
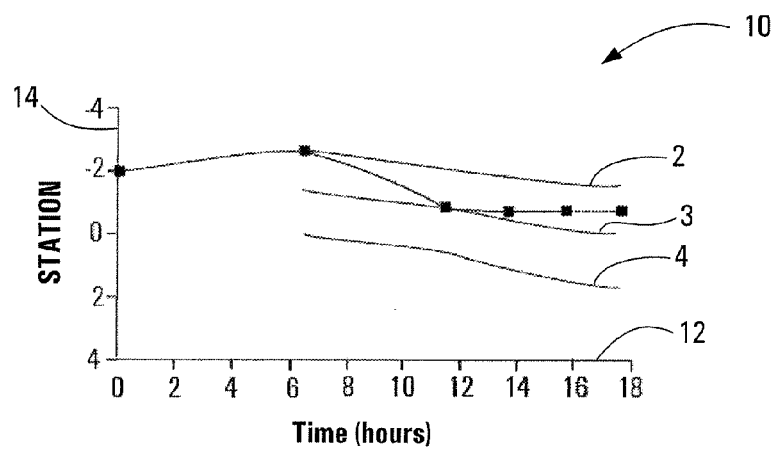
FIG. 6b shows a station curve conveying expected ranges of station (level of descent) versus time in accordance with another specific example of implementation of the present invention.

FIG. 6b of the drawings shows an alternative specific example of labor progress information conveyed in graphical format in accordance with another specific example of implementation. In the chart 10 depicted in FIG. 6b, horizontal axis 12 is associated to time and vertical axis 14 is associated to levels of descent, in this example expressed in the form of stations. The observed levels of descent at given times is plotted on the chart 10. The chart 10 also shows the expected ranges of levels of descent corresponding to the different times that are derived from information stored in memory unit 220. More specifically, curves defining an upper boundary 2 and a lower boundary 4 convey the ranges of expected levels of descent at various times. Optionally, the mean value of the level of descent is also shown in the chart 10 as a curve 3. At each time interval, the expected range of levels of descent is computed on the basis of the observed cervical dilation at that time using the information stored in memory unit 220.

In a second specific example of implementation, the labor progress generation module 210 is adapted to generate data for causing labor progress information to be conveyed in text format to a user. Any suitable representation for conveying the observed level of descent indicator in relation to the expected range of levels of descent may be used. In a non-limiting example, this information is represented in the form of a table conveying an observed level of descent in relation to the expected range of levels of descent for a cervical dilation measure.

| Observed Cervical dilation | Expected level of descent (station) | Observed level of descent (station) |
|---|---|---|
| 0 cm | Average: −2.23<br>Range: −0.10 to −4.35 | −2 |
| 1 cm | Average: −2.03<br>Range: −0.40 to −3.66 | No measure taken |
| 2 cm | Average: −1.85<br>Range: −0.42 to −3.28 | −1.5 |
| 3 cm | Average: −1.67<br>Range: −0.24 to −3.11 | −1.3 |
| 4 cm | . . . | |
| 5 cm | . . . | |
| . . . | . . . | |

It will be appreciated that other suitable manners for conveying an observed level of descent in relation to an expected range of levels of descent for a cervical dilation measure in a text format may be used without detracting from the spirit of the invention.

Advantageously, the information in the above-described table can be used by a physician or other health care practitioner to assess whether the baby is descending properly during labor.

Optionally, the above-described process and system can be used in combination with a system allowing assessing the progression of the cervical dilation during labor.

Figure 8:
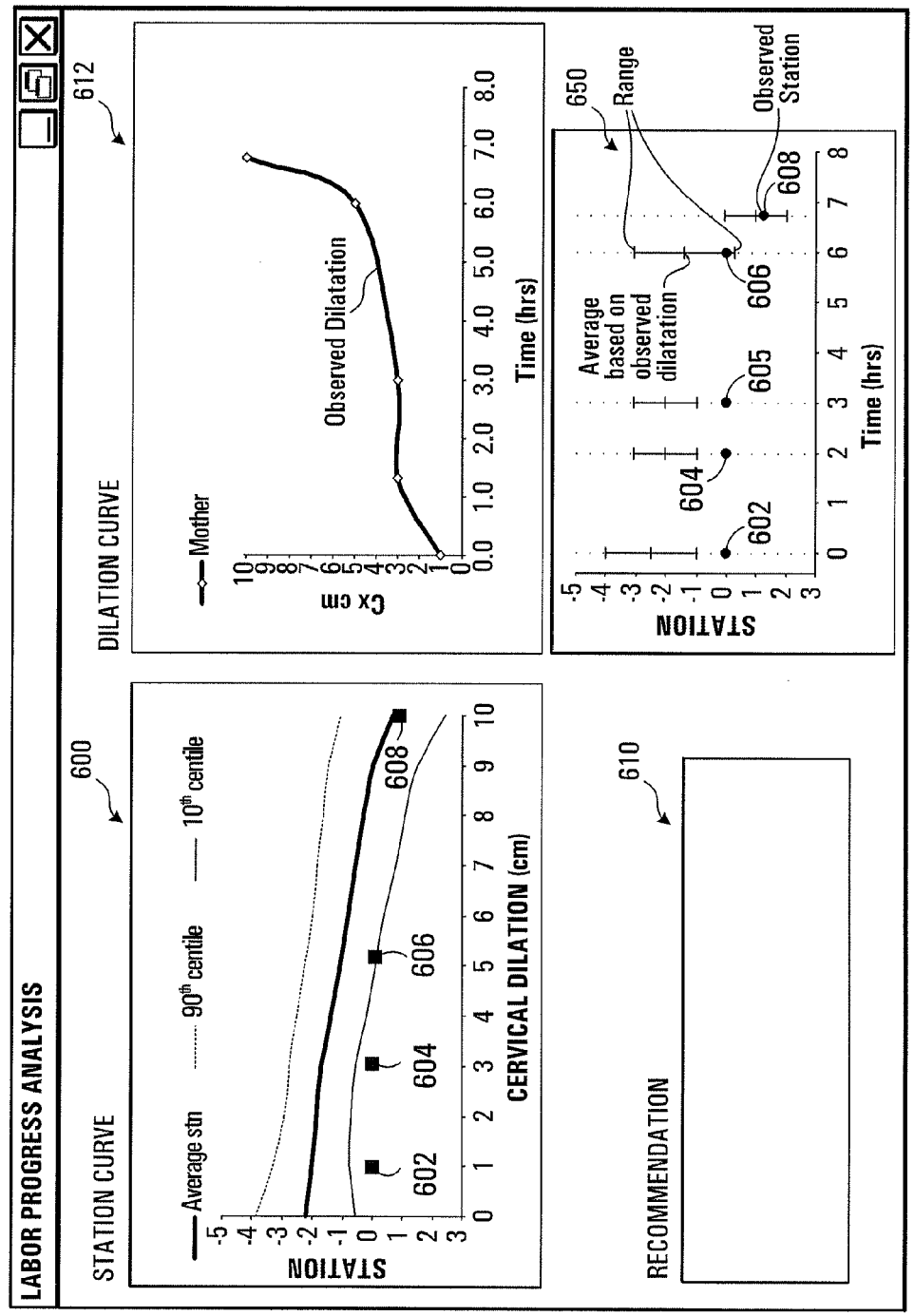
FIG. 8 shows an example of a graphical user interface including a visual representation of the data released by the processing unit shown in FIG. 1 in accordance with a specific example of implementation of the present invention.

FIG. 8 shows a non-limiting example of a specific visual representation caused to be displayed by output unit 106 when the system 100 depicted in FIG. 1 is used in combination with a system depicting the progress of the cervical dilation. This visual representation includes a first chart 600 conveying the observed levels of descent 602 604 606 608 with respect to expected ranges of levels of descent derived in accordance with the method described above. The specific visual representation shown in FIG. 6 also includes a second chart 612 conveys the progression of the cervical dilation during labor over time. In addition to, or instead of, chart 600, the specific visual representation includes chart 650 conveying the observed levels of descent 602 604 605 606 608 with respect to expected ranges of levels of descent plotted against the time axis. The expected ranges of levels of descent are derived on the basis of the observed cervical dilation depicted in chart 612. Optionally, the time axis of charts 612 and 650 are aligned with one another such as to allow a user to readily view the observed cervical dilation simultaneously with the observed level of descent against the expected the expected range of levels of descent at a given time.

By providing the physician with information related to the progression of the cervical dilation as well as with information regarding how the descent of the baby is progressing with respect to the cervical dilation, an improved assessment of labor progression can be provided to the physician or health care practitioner.

Optionally, as shown in the example depicted in FIG. 8, a recommendation component 610 is also displayed. The recommendation component provides an interpretation of the information displayed in charts 600 and 612 as well as a recommended course of action.

It will be appreciated that the specific visual representation shown in FIG. 8 has been provided for the purpose of illustration only and that other visual representations are possible, including additional items of information or omitting certain items of information, without detracting from the spirit of the invention.

Output Control Module 240

With reference to FIG. 4, the output control module 240 receives the labor progress information, and optionally the intervention policy information, and generates a signal to be released at output 114 for causing output unit 106 to convey information to a user. The output control module 240 will typically include components such as display drivers, printer drivers and user interface software components amongst others.

In a non-limiting implementation, the output control module 240 is adapted for generating a visual representation of the labor progress information in the form of a graphical window that could be shown on the display screen of a computer, PDA or other suitable device. Alternatively, the visual representation may be in the form of a printout. Optionally, the output control module 240 is further adapted for displaying the intervention policy information in a graphical format, or by using a coded colour scheme, or other display convention.

The specific manner in which the output control module 240 is implemented is not critical to the invention and as such will not be described further here.

Memory Unit 220

The content of memory unit 220 and the manner in which such content can be generated will now be described.

The memory unit 220 includes information conveying a plurality of expected ranges of levels of descent, each expected range of levels of descent corresponding to a respective cervical dilation. In a specific example of implementation, the mapping between the cervical dilations and the expected range of levels of descent is derived on the basis of actual clinical measurements taken from patients in the first stage of labor.

The information in memory unit 220 may be stored in any suitable format. In a first specific implementation, the information in memory unit 220 is stored as a table mapping cervical dilations to corresponding expected ranges of levels of descent. A specific example of such a table is illustrated below. In the table below, for each 1 cm increment of cervical dilation, a lower limit of the range of expected levels of descent and an upper limit of the range of expected levels of descent are provided as well as a mean value of the expected level of descent.

TABLE 1

| Cervical Dilatation | Expected Level of Descent (Station) | | | | | |
|---|---|---|---|---|---|---|
| | average | 95th centile | 5th centile | 90th centile | 10-th centile | StdDev |
| 0 | −2.23 | −4.35 | −0.10 | −3.88 | −0.57 | 1.29 |
| 1 | −2.03 | −3.66 | −0.40 | −3.30 | −0.76 | 0.99 |
| 2 | −1.85 | −3.28 | −0.42 | −2.96 | −0.73 | 0.87 |
| 3 | −1.67 | −3.11 | −0.24 | −2.79 | −0.55 | 0.87 |
| 4 | −1.37 | −2.86 | 0.12 | −2.53 | −0.21 | 0.90 |
| 5 | −1.08 | −2.58 | 0.42 | −2.25 | 0.09 | 0.91 |
| 6 | −0.81 | −2.33 | 0.71 | −2.00 | 0.37 | 0.92 |
| 7 | −0.54 | −2.25 | 1.17 | −1.88 | 0.79 | 1.04 |
| 8 | −0.28 | −2.04 | 1.47 | −1.65 | 1.09 | 1.07 |
| 9 | 0.02 | −1.90 | 1.94 | −1.48 | 1.51 | 1.17 |
| 10 | 0.66 | −1.59 | 2.91 | −1.09 | 2.42 | 1.37 |

It is to be appreciated that the values listed above are presented for the purpose of illustration only. Specific implementations of the invention may make use of values differing from the above without detracting from the spirit of the invention.

The mapping of the cervical dilations and the expected range of levels of descent may be derived in a number of manners. Below two different specific examples of methods for deriving the mapping are described. The first method is based on actual observations of the mean expected value of the level of descent and the standard deviation of the levels of descent. The second method is based on a mathematical model including:

1. A first mathematical equation describing a mapping between the mean expected value of the level of descent and the cervical dilation; and
2. A second mathematical equation describing a mapping between the standard deviation of the levels of descent and the levels of descent.

First Method

In a specific implementation, a range of expected levels of descent for each cervical dilation is derived on the basis of statistical observations obtained from a reference population. The table below shows in a summarized form the basic data used for deriving a mapping of level of descent versus dilatation. The numerical values presented below were obtained for nullipara women. It will be readily appreciated that similar data may be obtained for multipara women. Alternatively, a same set of data may be used for all women irrespective of whether they are nulliparous or multiparous.

TABLE 2

| Dilatation | no. of observations | average stn | StdDev |
|---|---|---|---|
| 0 | 252 | −2.2 | 1.3 |
| 1 | 952 | −2.0 | 1.0 |
| 2 | 1158 | −1.8 | 0.9 |
| 3 | 2930 | −1.7 | 0.9 |
| 4 | 2507 | −1.4 | 0.9 |
| 5 | 1554 | −1.1 | 0.9 |
| 6 | 1208 | −0.8 | 0.9 |
| 7 | 928 | −0.5 | 1.0 |
| 8 | 963 | −0.3 | 1.1 |
| 9 | 1416 | 0.0 | 1.2 |
| 10 | 3037 | 0.7 | 1.4 |

The above table includes, for each 1 cm increment of cervical dilation, the average of the observed levels of descent and the standard deviation of the observed levels of descent. By knowing the average level of descent and the distribution of values around the average level of descent, a relationship between a cervical dilation and a range of levels of descent can be constructed. For example, the outer limits of the range of levels of descent for each cervical dilation can be set to correspond to certain desired percentiles using the standard deviation. In a non-limiting example of implementation, the assumption that the observations of the levels of descent exhibit a generally normal distribution has been made. The person skilled in the art will appreciate that the distribution of values around the average level of descent may exhibit other types of distribution than the normal distribution without detracting from the spirit of the invention.

Figure 7A:
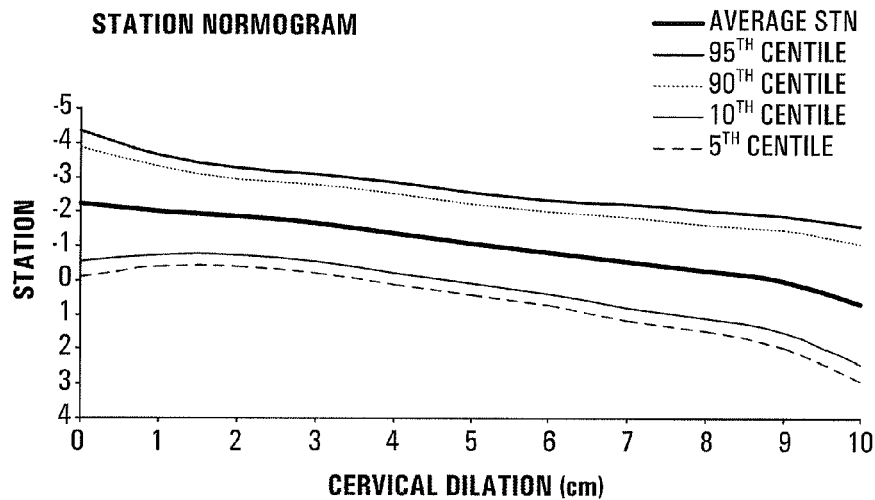
FIG. 7a shows a first non-limiting example of a normogram of stations (levels of descent) derived on the basis of actual observations in a reference populations in accordance with a specific example of implementation of the present invention.

FIG. 7a of the drawings is a graph depicting a mapping between the cervical dilations and expected ranges of levels of descent. In the figure shown, the ranges are defined by the outer limits corresponding to the $5^{th}$, $10^{th}$, $90^{th}$ and $95^{th}$ percentiles.

Second Method

In an alternative specific implementation, a mathematical model is used to derive a range of expected levels of descent for each cervical dilation. Many possible mathematical functions can be used to provide this mapping. In a non-limiting implementation, a first mathematical equation is used for deriving the mean expected level of descent for a given cervical dilation and a second mathematical model is used for deriving the standard deviation for the expected level of descent for each cervical dilation.

These mathematical equations may be derived using well-known statistical methods. In a non-limiting implementation, as a first step, well-known statistical methods are applied to the data shown in table 2 above in order to derive a curve that will fit the data describing the relationship between the average level of descent and the cervical dilation. Such statistical methods include, without being limited to, linear regression, polynomial approximation and any other mathematical method suitable for deriving a mathematical relationship between two variables. The specific mathematical equation below was derived by fitting a curve to the data of the average level of descent v. cervical dilation shown in table 2 above:

$$y=-0.012x^2+-0.1537x-2.2064$$

$$R^2=0.9944$$

In the above equation, y is the expected average (mean) level of descent, x is the cervical dilation and $R^2$ is the correlation coefficient squared which is a measure of how well the fit is between the curve defined by the mathematical equation and the actual observed data set out in the table above. As will be appreciated by the person skilled in the art, the closer $R^2$ is to "1" the better the fit of the mathematical model to the actual observations. In biological systems, an $R^2$ greater than about 0.65 is generally considered to be a good fit. The above-described equation provides a mapping between the expected mean levels of descent (stations) and the cervical dilations.

In a non-limiting implementation, as a second step, in order to obtain a range of levels of descent for a given cervical dilation, a second mathematical equation is derived mapping the standard deviation of the level of descent to the level of descent. Any suitable statistical model may be used without detracting from the spirit of the invention. The specific mathematical equation below was derived by fitting a curve to the data of the standard deviation of the level of descent v. cervical dilation shown in table 2 above:

$$y=0.1632x^2+0.3673x+1.1171$$

$$R^2=0.7517$$

In the above equation, y is the standard deviation of the level of descent, x is the level of descent and $R^2$ is the correlation coefficient squared which is a measure of how well the fit is between the curve defined by the mathematical equation and the actual observed data set out in table 2 above. FIG. 7c of the drawings is a graph depicting a mapping between the standard deviations of the levels of descent and level of descent on the basis of the above equation as well as the actual observed standard deviation of the level of descent set out in table 2 above.

Figure 7B:
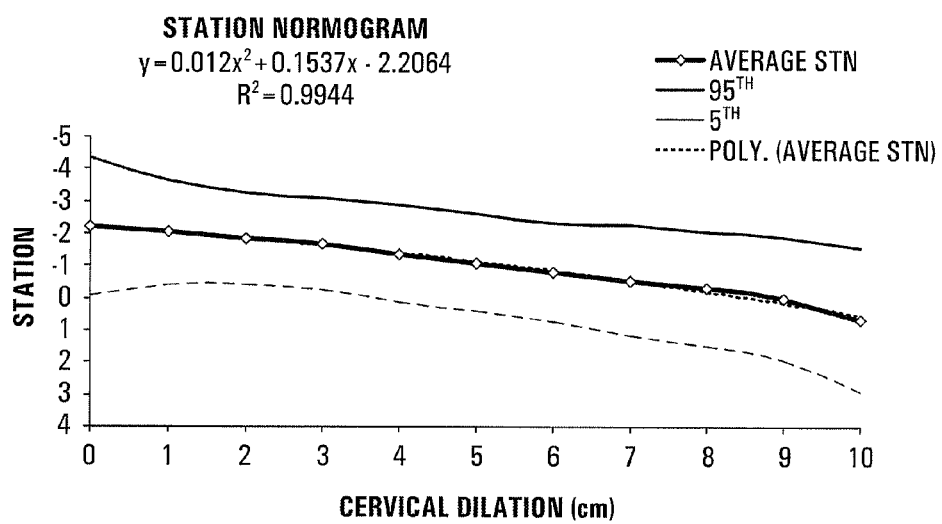
FIG. 7b shows a second non-limiting example of a normogram of stations (levels of descent) in accordance with a specific example of implementation of the present invention.
Figure 7C:
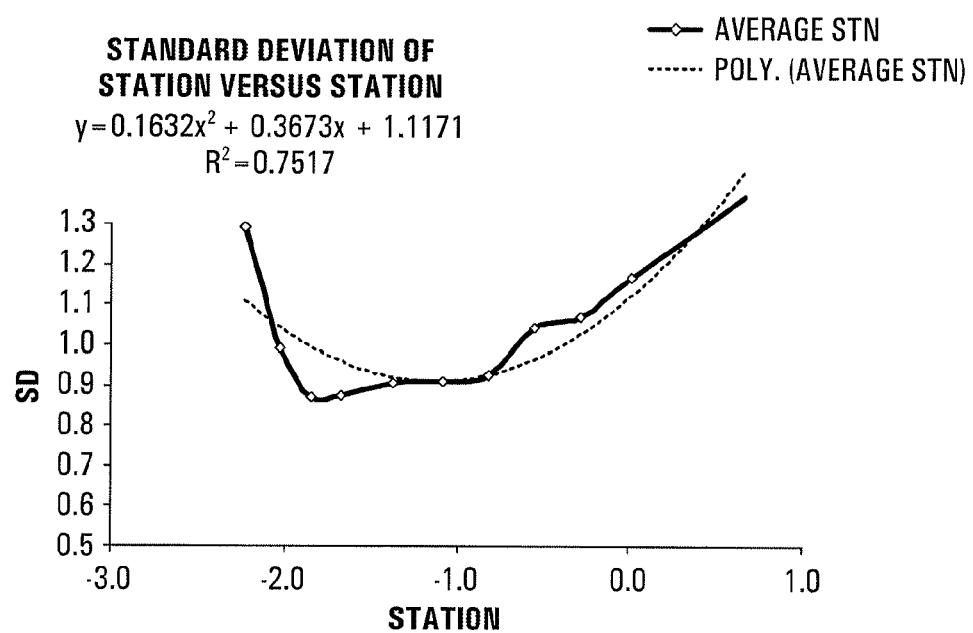
FIG. 7c is a graph depicting the average values for the standard deviation of stations based on observations and the corresponding mathematical model for the standard deviation of the stations in accordance with a specific example of implementation of the present invention.

FIG. 7b of the drawings is a graph depicting a mapping between expected ranges of levels of descent and cervical dilations on the basis of the above equations. It is to be appreciated that the values used in the above equations have been presented for the purpose of illustration only. Specific implementations of the invention may make use of values differing from the above without detracting from the spirit of the invention.

As a variant, memory unit 220 includes multiple sets of mappings between the cervical dilations and the expected range of levels of descent, each set of mappings being associated to mothers having certain characteristics. In a non-limiting example of implementation, a first set of mappings is provided for nulliparous women and a second set of mappings is provided for multiparous women. In another non-limiting example of implementation, a first set of mappings is provided for women between the ages of 20-30 and a second set of mappings is provided for women over 30. It will be readily apparent that other characteristics may be used either individually or in combination in order to differentiate between multiple sets of mappings between the cervical dilations and the expected range of levels of descent. Such characteristics include, without being limited to mother's weight, height, race and whether or not an epidural was given.

Second Embodiment

In a second specific embodiment, the processing unit 104 is adapted to derive an expected range of levels of descent at least in part on the basis of a cervical dilation measure, the cervical dilation measure being an expected cervical dilation measure. The expected cervical dilation is the dilation expected to be observed for a patient experiencing labor. The expected cervical dilation is derived on the basis of a set of clinical measurements associated with a patient. Any suitable method for deriving an expected cervical dilation may be used. In a non-limiting implementation, the expected cervical dilation is derived on the basis of the process described in U.S. Pat. No. 6,423,016 issued Jul. 23, 2002 to Hamilton, et al. and entitled "System and method for evaluating labor progress during childbirth". The contents of this document are incorporated herein by reference. The above referenced patent describes, amongst others a method for calculating an expected cervical dilation on the basis of a set of clinical measurements including a measurement of a previous dilatation of the cervix, a contraction count, a previous level of descent of the child, a previous effacement measurement of the cervix, an epidural status, and a parity status. The clinical measurements are processed to generate an expected dilatation of the cervix by taking a linear combination of the clinical measurements.

Figure 9:
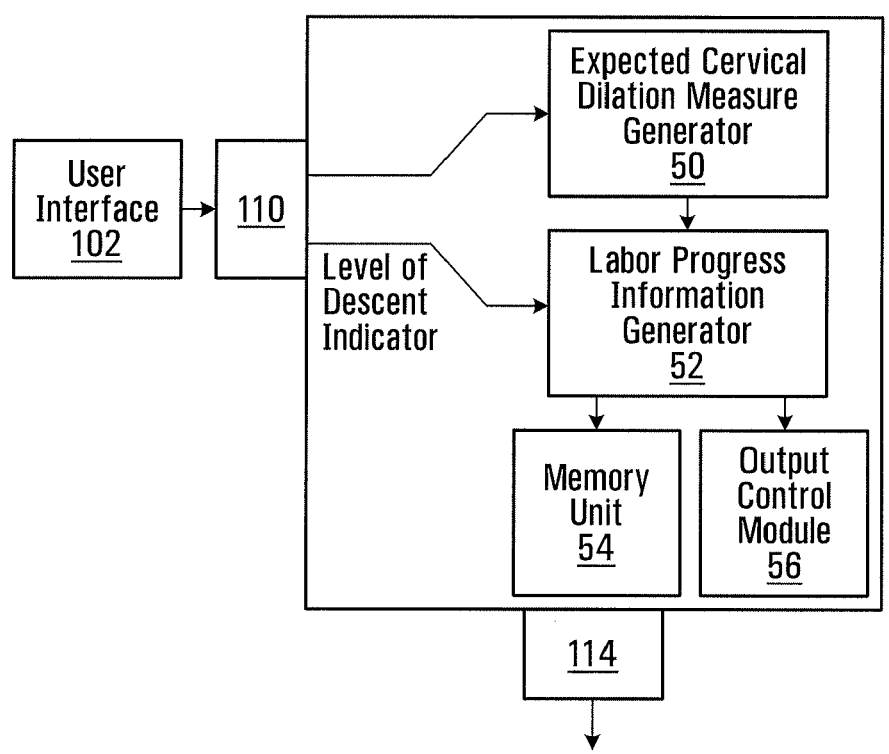
FIG. 9 shows a functional block diagram of an apparatus for generating labor progress information suitable for use in the system depicted in FIG. 1 in accordance with a second specific example of implementation of the present invention.

With reference to FIG. 9, the processing unit 104, in accordance with a second specific embodiment, includes an expected cervical dilation measure generator 50, labor progress generation module 52, a memory unit 54 and an output control module 56.

Memory unit 54 stores a plurality Of expected ranges of levels of descent, each expected range of levels of descent corresponding to a respective cervical dilation. Memory unit 54 can be implemented in a manner similar to that described in connection with memory unit 220 and as such will not be described further here. It will be appreciated that although memory unit 54 has been shown to be an integral part of processing unit 104, memory unit 54 may be an external component to processing unit 104 without detracting from the spirit of the invention.

The output control module 56 receives the labor progress information, and optionally the intervention policy information, and generates a signal to be released at output 114 for causing output unit 106 to convey information to a user. The output control module 56 can be implemented in a manner similar to that described in connection with output control module 240 and as such will not be described further here.

The expected cervical dilation measure generator 50 receives from input 110 a set of clinical measurements associated with a patient and is adapted to derive an expected cervical dilation. In a non-limiting implementation, the expected cervical dilation is derived on the basis of the process described in U.S. Pat. No. 6,423,016 issued Jul. 23, 2002 to Hamilton, et al. and entitled "System and method for evaluating labor progress during childbirth". The clinical measurements are processed to generate an expected future dilatation of the cervix by taking a linear combination of the clinical measurements. The expected cervical dilation measure generator 50 is adapted to release the expected cervical dilation for transmission to the labor progress information generation unit 52.

Optionally, (not shown in the drawing) the expected cervical dilation measure generator 50 also releases a signal for causing the expected cervical dilation to be conveyed to a user in a graphical format. Examples of the manner in which the expected cervical dilation may be displayed are described in U.S. Pat. No. 6,423,016.

The labor progress information generation unit 52 receives an observed level of descent indicator from input 110 and an expected cervical dilation measure from the expected cervical dilation measure generator 50. The labor progress information generation unit 52 generates data conveying whether the observed level of descent indicator is within the expected range of levels of descent corresponding to the expected cervical dilation. The expected range of levels of descent corresponding to the cervical dilation is derived from information stored in memory unit 54. The expected range of levels of descent is derived in the same manner as that described above with reference to labor progress information generation unit 210 (shown in FIG. 4) by substituting the observed cervical dilation measure received at input 110 with the expected cervical dilation measure received from the expected cervical dilation measure generator 50.

In a first specific example of implementation, the labor progress generation module 52 is adapted to generate data for causing labor progress information to be conveyed in graphical format.

Figure 10A:
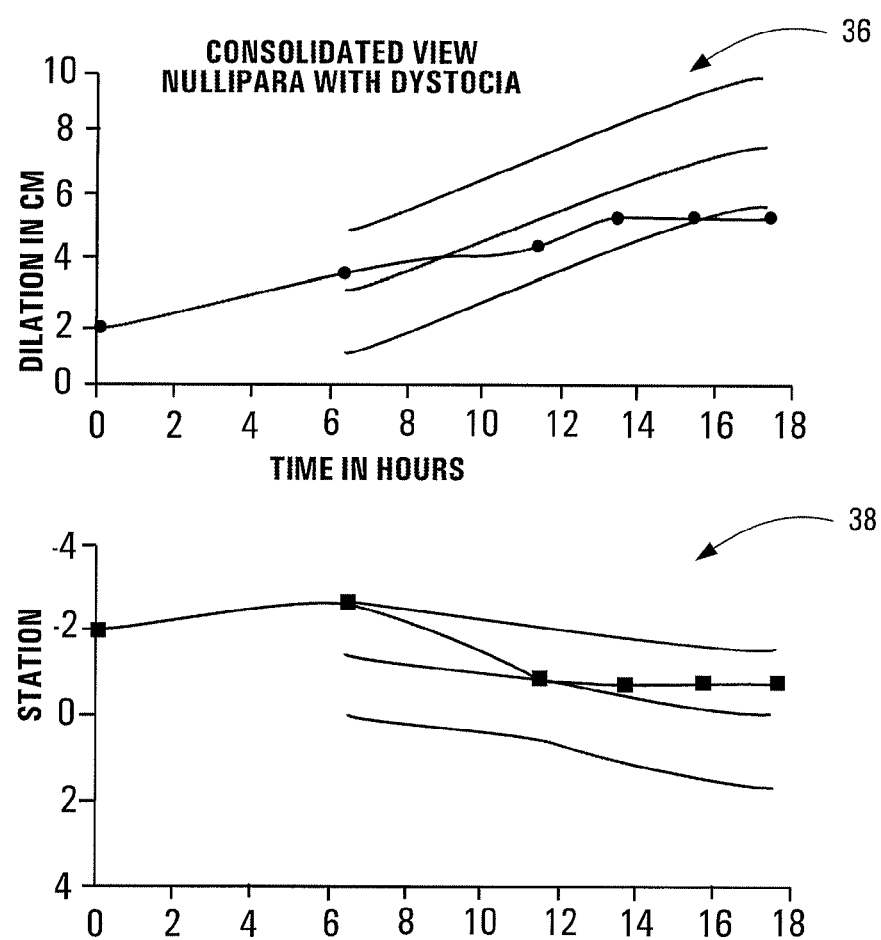
FIGS. 10a and 10b show examples of visual representations of the data released by the apparatus for generating labor progress information shown in FIG. 9 in accordance with a specific example of implementation of the present invention.
Figure 10B:
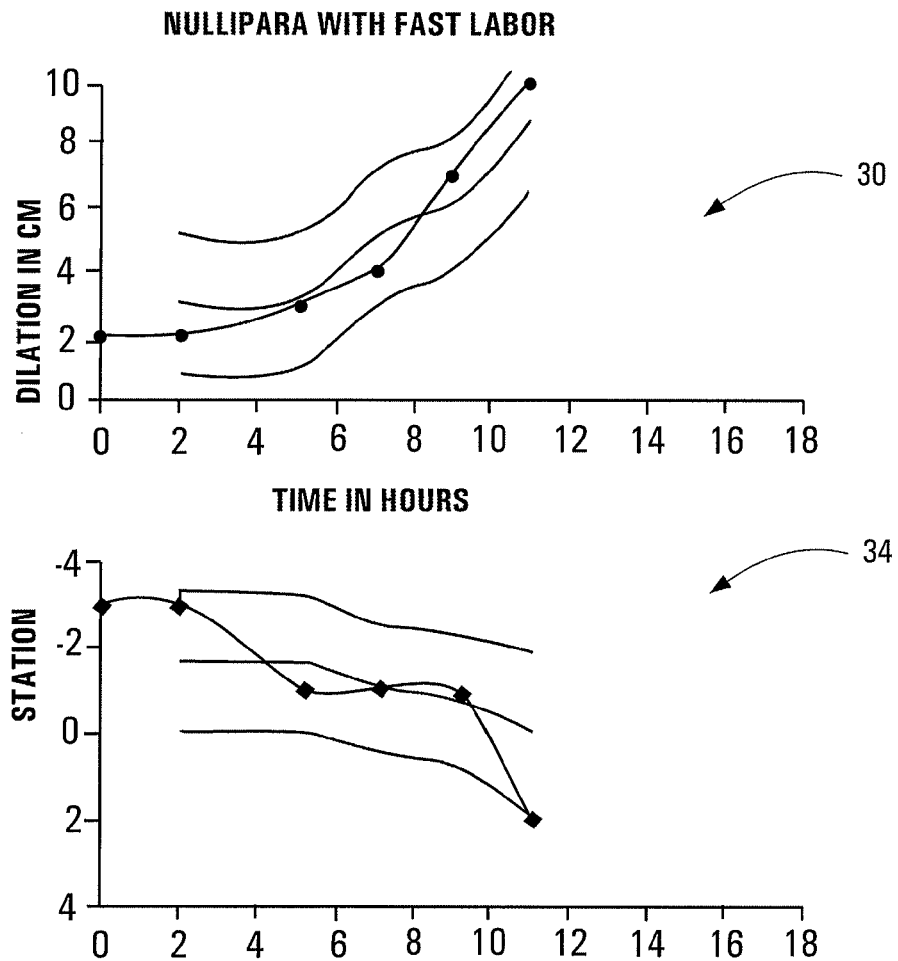

FIGS. 10a and 10b of the drawings show two (2) practical examples of labor progress information conveyed in graphical format in accordance with a specific example of implementation. The example depicted in FIG. 10a is associated with a birth with dystocia and the example depicted in FIG. 10b is associated with a birth where the labor was faster than average.

With reference to FIG. 10a, there is depicted a first chart 36 showing the progression of the cervical dilation plotted against time as swell as a range of expected cervical dilations plotted against time for a birth with dystocia. This information is generated by the expected cervical dilation measure generator 50. In the first chart 36, the horizontal axis is associated to time and the vertical axis is associated to cervical dilations. A second chart 38 is also depicted showing the progression of the level of descent plotted against time as well as a range of expected levels of descent plotted against time. The range of expected levels of descent at a given time is derived at least in part on the basis of the expected cervical dilation associated with the same given time. In the second chart 38, the horizontal axis is associated to time and the vertical axis is associated to levels of descent. As can be seen in the charts shown in FIG. 10a, as time progresses both the observed dilatation and observed descent are becoming progressively more unfavorably deviant from the expected dilation and descent, thereby indicating a growing abnormality in this labor.

With reference to FIG. 10b, there is depicted a first chart 30 showing the progression of the cervical dilation plotted against time as swell as a range of expected cervical dilations plotted against time for a fast labor. This information is generated by the expected cervical dilation measure generator 50. In the first chart 30, the horizontal axis is associated to time and the vertical axis is associated to cervical dilations. A second chart 34 is also depicted showing the progression of the level of descent plotted against time as swell as a range of expected levels of descent plotted against time. The range of expected levels of descent at a given time is derived at least in part on the basis of the expected cervical dilation associated with the same given time. In the second chart 34, the horizontal axis is associated to time and the vertical axis is associated to levels of descent. As can be seen from the charts shown in FIG. 10b, as time progresses both the observed dilatation and descent are becoming progressively more favorably deviant from the expected dilation and descent, thereby indicating that this labor is proceeding faster than most women under the same circumstances who are experiencing similar labor conditions.

As depicted in FIGS. 10a and 10b, the time axis are aligned with one another such as to allow a user to readily view the observed cervical dilation/observed level of descent against the range expected cervical dilation and the range of levels of descent at a given time.

Advantageously, the information conveyed by the charts in FIGS. 10*a* and 10*b* can be used by a physician or other health care practitioner to assess whether the baby is descending through the birth canal normally during labor and whether the cervical dilation is progressing normally.

In an alternative implementation, the labor progress generation module 52 is adapted to generate data for causing labor progress information to be conveyed in text format to a user. Any suitable representation for conveying the observed level of descent indicator in relation to the expected range of levels of descent may be used.

Optionally, (not shown in FIGS. 10*a* and 10*b*) a recommendation data element is also provided to the user. The recommendation component provides an interpretation of the information displayed in charts 30 34 or 36 38 as well as a recommended course of action.

It will be appreciated that the specific visual representations shown in FIGS. 10*a* and 10*b* have been provided for the purpose of illustration only and that other visual representations are possible, including additional items of information or omitting certain items of information, without detracting from the spirit of the invention.

Non-Limiting Specific Practical Implementations

Those skilled in the art should appreciate that in some embodiments of the invention, all or part of the functionality for evaluating labor progress during childbirth for an obstetrics patient previously described herein with respect to the apparatus 101, may be implemented as pre-programmed hardware or firmware elements (e.g., application specific integrated circuits (ASICs), electrically erasable programmable read-only memories (EEPROMs), etc.), or other related components.

In other embodiments of the invention, all or part of the functionality previously described herein with respect to the apparatus 101 (shown in FIG. 1) for evaluating labor progress during childbirth may be implemented as software consisting of a series of instructions for execution by a computing unit. The series of instructions could be stored on a medium which is fixed, tangible and readable directly by the computing unit, (e.g., removable diskette, CD-ROM, ROM, PROM, EPROM, flash memory or fixed disk), or the instructions could be stored remotely but transmittable to the computing unit via a modem or other interface device (e.g., a communications adapter) connected to a network over a transmission medium. The transmission medium may be either a tangible medium (e.g., optical or analog communications lines) or a medium implemented using wireless techniques (e.g., microwave, infrared or other transmission schemes).

Figure 11:
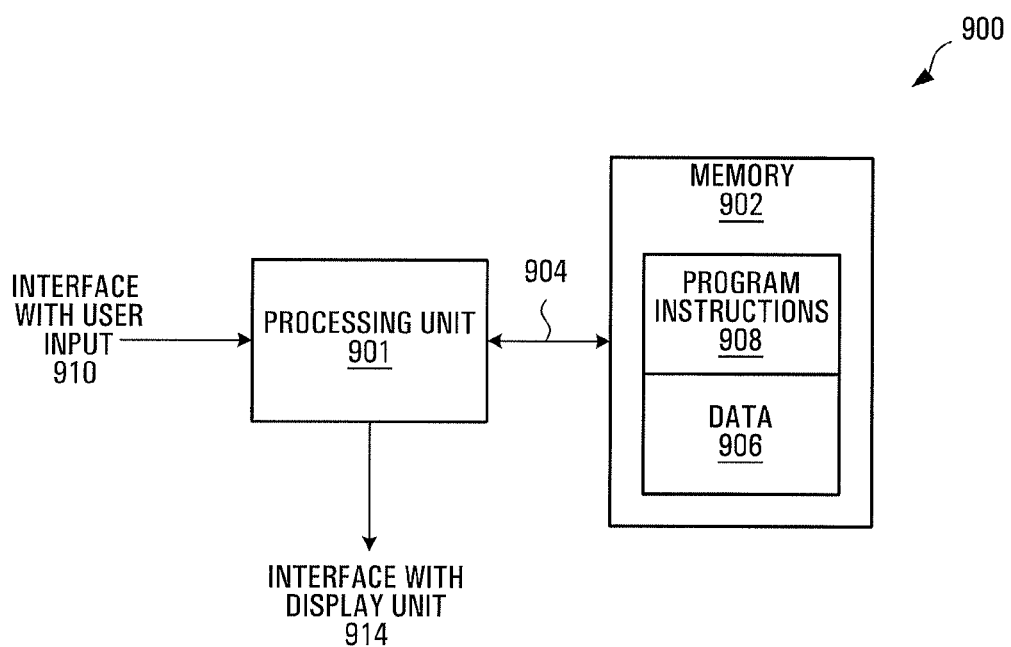
FIG. 11 shows a functional block diagram of an apparatus for generating labor progress information associated to an obstetrics patient in accordance with another specific example of implementation of the present invention.

The apparatus 101 for evaluating labor progress during childbirth may be configured as a computing unit 900 of the type depicted in FIG. 11, including a processing unit 901 and a memory 902 connected by a communication bus 904. The memory 902 includes data 906 and program instructions 908. The processing unit 901 is adapted to process the data 906 and the program instructions 908 in order to implement the method described in the specification and depicted in the drawings. The computing unit 900 may also comprise a number of interfaces 910, and 914 for receiving or sending data elements to external devices. For example, interface 910 receives signals from user interface 102 as described with respect to FIG. 1, and as such is used for receiving information data elements associated to an obstetrics patient. The processing unit 901 is operative for processing the information data elements to generate labor progress information associated to the obstetrics patient, the labor progress information conveying whether the level of descent indicator is within an expected range of levels of descent for a given cervical dilation measure. Optionally, the processing unit 901 is operative for generating intervention policy information when the level of descent indicator is outside the expected range of levels of descent. Interface 914 is for releasing a signal conveying the labor progress information, an optionally the intervention policy information. The released signal is transmitted to output unit 106 (FIG. 1), such that output unit 106 may convey the labor progress information generated by processing unit 901 to a health care professional.

In a specific example of implementation, the memory 902 includes a program element within the program instructions 908, for execution by the computing unit 900. Once the processing unit 901 has derived labor progress information associated to the obstetrics patient, the program element is operative cause the labor progress information to be conveyed to a user on an output unit. As described above, in specific embodiment, the output unit 106 can include either one of a display screen or a printer.

In a specific implementation, the data portion 906 of the memory 902 includes data conveying a plurality of expected ranges of levels of descent, each expected range of levels of descent corresponding to a respective cervical dilation.

Figure 12:
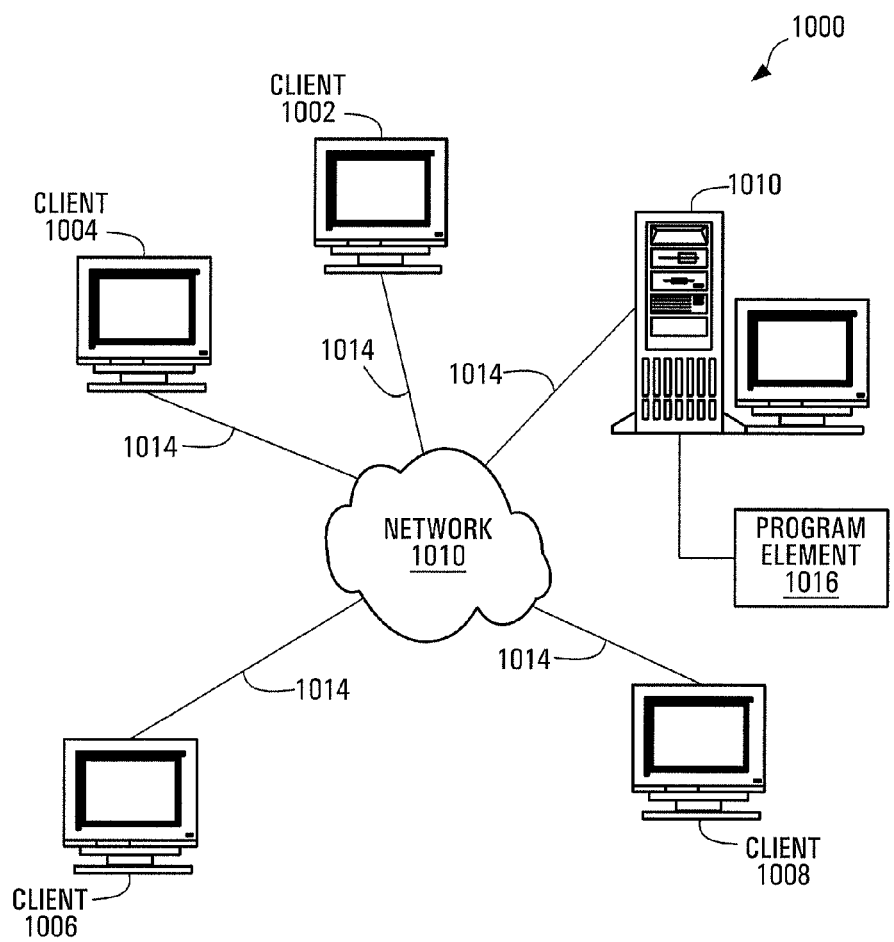
FIG. 12 shows a functional block diagram of a client-server system for generating labor progress information associated to an obstetrics patient in accordance with an alternative specific example of implementation of the present invention.

It will be appreciated that the system for monitoring an obstetrics patient may also be of a distributed nature where the set of information data elements associated to an obstetrics patient is collected at one location or more locations and transmitted over a network to a server unit implementing the method described above. The server unit may then transmits a signal for causing an output unit to convey information to the user. The output unit may be located in the same location where the set of information data elements is being obtained or in the same location as the server unit or in yet another location. FIG. 12 illustrates a network-based client-server system 1000 for monitoring an obstetrics patient associated to one or more obstetrics patients. The client-server system 1000 includes a plurality of client systems 1002, 1004, 1006 and 1008 connected to a server system 1010 through network 1012. The communication links 1014 between the client systems 1002, 1004, 1006 and 1008 and the server system 1010 can be metallic conductors, optical fibres or wireless, without departing from the spirit of the invention. The network 1012 may be any suitable network including but not limited to a global public network such as the Internet, a private network and a wireless network. The server 1010 may be adapted to process and issue signals concurrently using suitable methods known in the computer related arts.

The server system 1010 includes a program element 1016 for execution by a CPU. Program element 1016 implements similar functionality as program instructions 908 (shown in FIG. 11) and includes the necessary networking functionality to allow the server system 1010 to communicate with the client systems 1002, 1004, 1006 and 1008 over network 1012. In a non-limiting example of implementation, program element 1016 includes a number of program element components, each program element components implementing a respective portion of the functionality of apparatus 101 (shown in FIG. 1).

Figure 13:
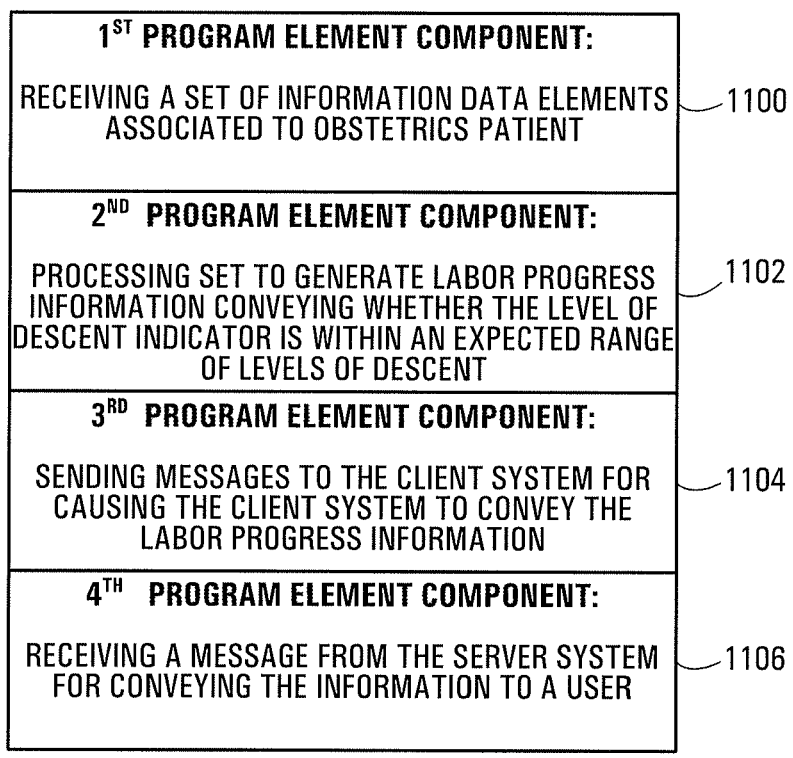
FIG. 13 is a conceptual representation of a computer readable storage medium storing a program element suitable for use in connection with the client-server system shown in FIG. 12 for generating labor progress information associated to an obstetrics patient in accordance with another specific example of implementation of the present invention.

FIG. 13 shows a non-limiting example of the architecture of an example of implementation of program element 1016 at the server system:

1. The first program element component 1100 is executed on server system 1010 and is for receiving a set of information data elements associated to an obstetrics patient. In a specific implementation, the set of information data elements includes a cervical dilation measure and a level of descent indicator.

2. The second program element component 1102 is executed on server system 1010 and is for processing the set of information data elements to generate labor progress information associated to the obstetrics patient. The labor progress information ranking data element conveys whether the level of descent indicator is within an expected range of levels of descent, the expected range of levels of descent corresponding to the cervical dilation measure.

3. The third program element component 1104 is executed on server system 1010 and is for sending messages to a client system (1002, 1004, 1006 or 1008) for causing the client system to convey the labor progress information.

4. The fourth program element component 1106 is executed on the client system and is for receiving a message from the server system 1010 for conveying the labor progress information to a user.

Those skilled in the art should further appreciate that the program instructions may be written in a number of programming languages for use with many computer architectures or operating systems. For example, some embodiments may be implemented in a procedural programming language (e.g., "C") or an object oriented programming language (e.g., "C++" or "JAVA").

Although the present invention has been described in considerable detail with reference to certain preferred embodiments thereof, variations and refinements are possible without departing from the spirit of the invention. Therefore, the scope of the invention should be limited only by the appended claims and their equivalents.

The invention claimed is:

1. A method for monitoring an obstetrics patient during childbirth, said method comprising:
   a) receiving a set of information data elements associated with the obstetrics patient, the set of information data elements conveying:
      i. a cervical dilation measure; and
      ii. an observed level of descent indicator;
   b) using a processing unit programmed with software, deriving an expected range of levels of descent at least in part by processing the cervical dilation measure, the derived expected range of levels of descent conveying levels of descent expected when childbirth is progressing normally; and
   c) causing labor progress information associated with the obstetrics patient to be displayed on a display device, the labor progress information conveying whether the observed level of descent indicator lies within the derived expected range of levels of descent.

2. A method as defined in claim 1, wherein the labor progress information conveys the observed level of descent indicator in relation to the expected range of levels of descent.

3. A method as defined in claim 2, wherein the cervical dilation measure is an expected cervical dilation measure associated with the obstetrics patient.

4. A method as defined in claim 3, wherein said method comprises processing the observed level of descent indicator to determine whether it lies within the expected range of levels of descent.

5. A method as defined in claim 1, wherein the labor progress information is caused to be conveyed in graphical format.

6. A method as defined in claim 5, wherein the graphical format includes a chart having a horizontal axis and a vertical axis, the horizontal axis being associated with time and the vertical axis being associated with levels of descent.

7. A method as defined in claim 2, wherein the cervical dilation measure is an observed cervical dilation measure associated with the obstetrics patient.

8. A method as defined in claim 7, wherein said method further comprises:
   providing a plurality of expected ranges of levels of descent, each expected range of levels of descent corresponding to a respective cervical dilation; and
   causing the plurality of expected ranges of levels of descent to be conveyed to a user.

9. A method as defined in claim 8, wherein the plurality of expected ranges of levels of descent is derived from data associated with a reference population.

10. A method as defined in claim 7, wherein the labor progress information is caused to be conveyed in graphical format.

11. A method as defined in claim 10, wherein the graphical format includes a chart having a horizontal axis and a vertical axis, the horizontal axis being associated with cervical dilation measures and the vertical axis being associated with levels of descent.

12. A method as defined in claim 1, said method further comprising:
   processing the observed level of descent indicator to determine whether it lies within the derived expected range of levels of descent;
   generating intervention policy information when the observed level of descent indicator is outside the expected range of levels of descent; and
   causing the intervention policy information to be provided to a user.

13. A method as defined in claim 1, wherein the labor progress information is caused to be conveyed in text format.

14. A method as defined in claim 1, wherein the display device is selected from the set consisting of a display screen and a printer.

15. A computer program product, tangibly stored on one or more tangible computer readable storage media, for monitoring an obstetrics patient during childbirth, the program product comprising instructions that, when executed, cause a programmable system including at least one programmable processor to perform operations, the operations comprising:
   i. receiving a set of information data elements associated with the obstetrics patient, the set of information data elements including:
      (1) a cervical dilation measure; and
      (2) an observed level of descent indicator;
   ii. deriving an expected range of levels of descent at least in part by processing the cervical dilation measure, the derived expected range of levels of descent conveying levels of descent expected when childbirth is progressing normally;
   iii. causing labor progress information associated with the obstetrics patient to be displayed on a display device, the labor progress information conveying whether the observed level of descent indicator lies within the derived expected range of levels of descent.

16. A computer program product as defined in claim 15, wherein the labor progress information conveys the observed level of descent indicator in relation to the expected range of levels of descent.

17. A computer program product as defined in claim 16, wherein the cervical dilation measure is an expected cervical dilation measure associated with the obstetrics patient.

18. A computer program product as defined in claim 17, wherein said operations further comprise processing the observed level of descent indicator to determine whether it lies within the expected range of levels of descent.

19. A computer program product as defined in claim 15, wherein the labor progress information is caused to be conveyed in graphical format.

20. A computer program product as defined in claim 19, wherein the graphical format includes a chart having a horizontal axis and a vertical axis, the horizontal axis being associated with time and the vertical axis being associated with levels of descent.

21. A computer program product as defined in claim 15, wherein the cervical dilation measure is an observed cervical dilation measure associated with the obstetrics patient.

22. A computer program product as defined in claim 21, wherein said operations further comprise:
   providing a plurality of ranges of levels of descent, each range of levels of descent corresponding to a respective cervical dilation; and
   causing the plurality of ranges of levels of descent to be conveyed to a user.

23. A computer program product as defined in claim 22, wherein the plurality of ranges of levels of descent conveys a reference band of expected levels of descent derived from data associated with a reference population.

24. A computer readable storage medium as defined in claim 21, wherein the labor progress information is caused to be provided in graphical format.

25. A computer readable storage medium as defined in claim 24, wherein the graphical format includes a chart having a horizontal axis and a vertical axis, the horizontal axis being associated with cervical dilation measures and the vertical axis being associated with levels of descent.

26. A computer readable storage medium as defined in claim 15, wherein said operations further comprise:
   a) processing the observed level of descent indicator to determine whether it lies within the derived expected range of levels of descent;
   b) generating intervention policy information when the observed level of descent indicator is outside the expected range of levels of descent; and
   c) causing the intervention policy information to be provided to a user.

27. A computer readable storage medium as defined in claim 15, wherein the labor progress information is caused to be provided in text format.

28. A computer readable storage medium as defined in claim 15, wherein the display device is selected from the set consisting of a display screen and a printer.

29. A system for monitoring an obstetrics patient during childbirth, comprising:
   a) an interface for receiving a set of information data elements associated with the obstetrics patient, the set of information data elements conveying:
      i. a cervical dilation measure; and
      ii. an observed level of descent indicator;
   b) an apparatus including:
      i. an input in communication with said interface for receiving the set of information data elements;
      ii. a processing unit in communication with said input, said processing unit being programmed for:
         (1) deriving an expected range of levels of descent at least in part by processing the cervical dilation measure, the derived expected range of levels of descent conveying levels of descent expected when childbirth is progressing normally;
         (2) generating a signal for causing labor progress information associated with the obstetrics patient to be displayed on a display device, the labor progress information conveying whether the observed level of descent indicator lies within the derived expected range of levels of descent.

30. A system as defined in claim 29, wherein the interface is selected from a keyboard, a pointing device, a touch sensitive screen, a data input device and a voice recognition unit.

31. A system as defined in claim 29, wherein said display device is either one of a display screen and a printing device.

32. A system as defined in claim 29, wherein the cervical dilation measure is an expected cervical dilation measure associated with the obstetrics patient.

33. A system as defined in claim 32, wherein said processing unit is programmed for processing the observed level of descent indicator to determine whether it lies within the expected range of levels of descent.

34. A system as defined in claim 29, wherein the cervical dilation measure is an observed cervical dilation measure associated with the obstetrics patient.

35. A method for monitoring an obstetrics patient during childbirth, said method comprising:
   a) obtaining a set of information data elements associated with the obstetrics patient, the set of information data elements conveying:
      i. a cervical dilation measure; and
      ii. an observed level of descent indicator;
   b) transmitting the set of information data elements to a remote computing apparatus, the remote computing apparatus being programmed for:
      i. deriving an expected range of levels of descent at least in part by processing the cervical dilation measure, the derived expected range of levels of descent conveying levels of descent expected when childbirth is progressing normally;
   c) receiving data from the remote computing apparatus, the data conveying labor progress information associated with the obstetrics patient, the labor progress information conveying whether the observed level of descent indicator lies within the derived expected range of levels of descent; and
   d) causing the labor progress information to be provided to a user using a display device.

* * * * *